United States Patent
Abe

(10) Patent No.: US 10,265,045 B2
(45) Date of Patent: Apr. 23, 2019

(54) MEDICAL DIAGNOSTIC IMAGING APPARATUS, IMAGE PROCESSING APPARATUS, AND IMAGE PROCESSING METHOD

(71) Applicant: Toshiba Medical Systems Corporation, Otawara-shi (JP)

(72) Inventor: Yasuhiko Abe, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 154 days.

(21) Appl. No.: 14/929,683

(22) Filed: Nov. 2, 2015

(65) Prior Publication Data

US 2016/0140711 A1    May 19, 2016

(30) Foreign Application Priority Data

Nov. 13, 2014   (JP) ................. 2014-230995

(51) Int. Cl.
*A61B 8/08* (2006.01)
*G06T 7/62* (2017.01)
(Continued)

(52) U.S. Cl.
CPC ........... *A61B 8/0883* (2013.01); *A61B 8/483* (2013.01); *A61B 8/485* (2013.01); *A61B 8/5223* (2013.01);
(Continued)

(58) Field of Classification Search
None
See application file for complete search history.

(56) References Cited

U.S. PATENT DOCUMENTS

| 6,873,718 B2* | 3/2005 | O'Donnell | G06T 7/0012 |
| | | | 382/131 |
| 8,983,160 B2* | 3/2015 | Chono | A61B 5/02028 |
| | | | 378/4 |

(Continued)

FOREIGN PATENT DOCUMENTS

JP    2004-202131    7/2004

OTHER PUBLICATIONS

Solaiyappan et al., "Interactive visualization for rapid noninvasive cardiac assessment", IEEE Computer Society, Computer vol. 29, Issue: 1, Jan. 1996, pp. 55-62.*

(Continued)

*Primary Examiner* — Matthew C Bella
*Assistant Examiner* — Jose Torres
(74) *Attorney, Agent, or Firm* — Oblon, McClelland, Maier & Neustadt, L.L.P.

(57) ABSTRACT

A medical diagnostic imaging apparatus according to an embodiment includes control circuitry. The control circuitry obtains three-dimensional medical image data of acquiring an area of an object. The control circuitry defines a setting region on the three-dimensional medical image data. The control circuitry divides the setting region into a region of interest and a region other than that by at least a single boundary position. The control circuitry generates, from the three-dimensional medical image data, an image in which the region of interest and the region other than that are distinguished from each other. The control circuitry calculates information about at least one of a volume of and a motion index of the region of interest. The control circuitry displays the calculated information for the region of interest in the image.

9 Claims, 7 Drawing Sheets

(51) Int. Cl.
  *G06F 19/00*  (2018.01)
  *G06T 19/20*  (2011.01)
  *G06T 7/246*  (2017.01)

(52) U.S. Cl.
  CPC .............. *G06F 19/00* (2013.01); *G06T 7/246* (2017.01); *G06T 7/62* (2017.01); *G06T 19/20* (2013.01); *G06T 2207/10136* (2013.01); *G06T 2207/30048* (2013.01); *G06T 2207/30104* (2013.01); *G06T 2210/41* (2013.01); *G06T 2219/2012* (2013.01); *G06T 2219/2021* (2013.01)

(56) References Cited

U.S. PATENT DOCUMENTS

| | | | | |
|---|---|---|---|---|
| 2004/0249282 | A1* | 12/2004 | Olstad | A61B 8/08 600/437 |
| 2008/0262814 | A1* | 10/2008 | Zheng | G06F 19/3437 703/11 |
| 2011/0313291 | A1* | 12/2011 | Chono | A61B 8/08 600/440 |
| 2012/0014588 | A1* | 1/2012 | Chono | A61B 8/00 382/133 |
| 2012/0281895 | A1* | 11/2012 | Chono | A61B 8/461 382/128 |
| 2014/0219524 | A1* | 8/2014 | Takeguchi | A61B 6/463 382/128 |
| 2015/0078640 | A1* | 3/2015 | Guo | G06T 7/0083 382/131 |
| 2015/0317799 | A1* | 11/2015 | Akahori | G06T 7/0081 382/128 |
| 2016/0093044 | A1* | 3/2016 | Okazaki | A61B 8/5207 382/131 |

OTHER PUBLICATIONS

Zheng et al., "Four-Chamber Heart Modeling and Automatic Segmentation for 3-D Cardiac CT Volumes Using Marginal Space Learning and Steerable Features", IEEE Transactions on Medical Imaging, vol. 27 No. 11, Nov. 2008, pp. 1668-1681.*

Mahapatra et al., "Cardiac LV and RV Segmentation Using Mutual Context Information", International Workshop on Machine Learning in Medical Imaging, MLMI 2002: Machine Learning in Medical Imaging, pp. 201-209.*

Tomoyuki Takeguchi, et al., "Practical considerations for a method of rapid cardiac function analysis based on three-dimensional speckle tracking in a three-dimensional diagnostic ultrasound system", Journal of Medical Ultrasonics in Medicine, 2009, 9 pgs.

Office Action dated Jun. 26, 2018 in Japanese Patent Application No. 2014-230995.

* cited by examiner

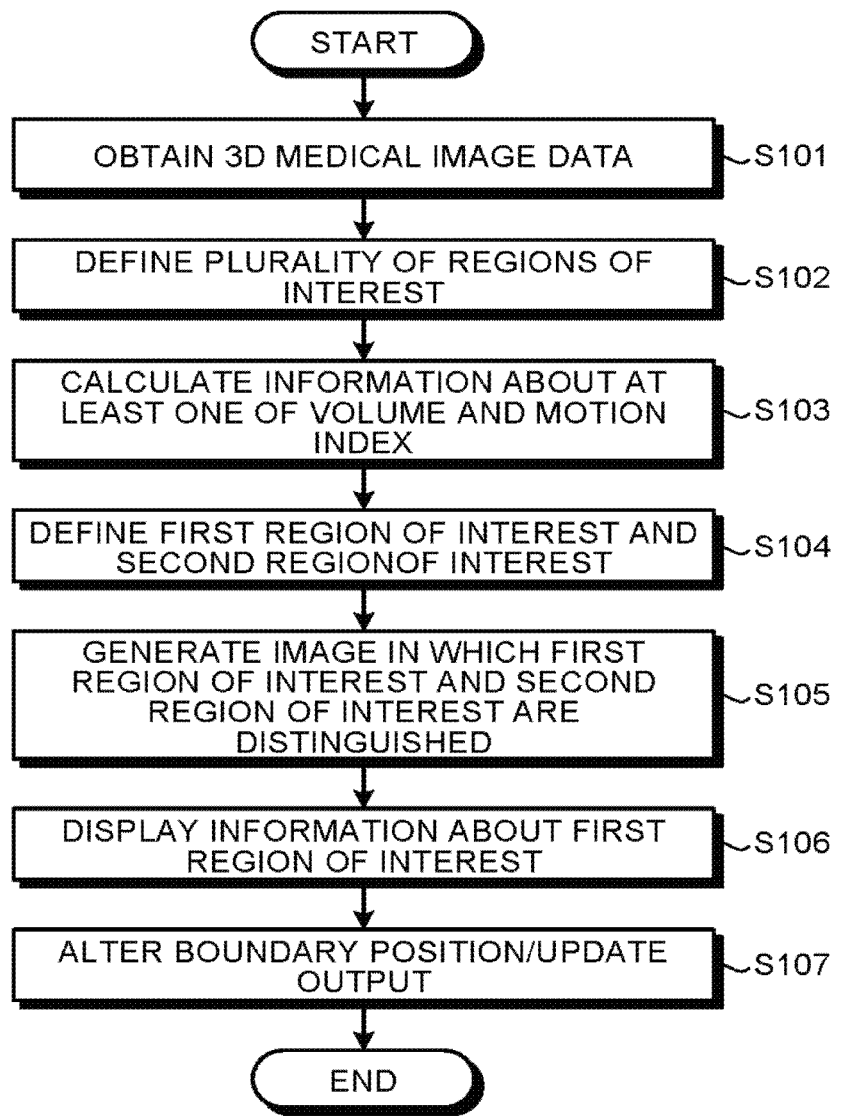

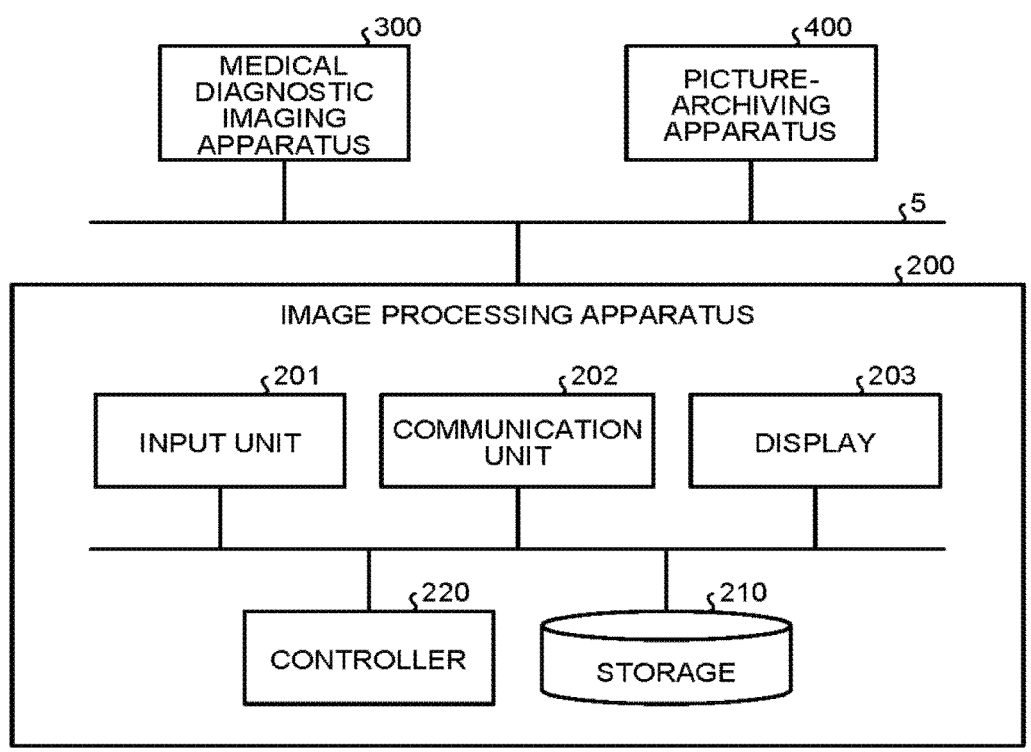

MEDICAL DIAGNOSTIC IMAGING APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2014-230995, filed on Nov. 13, 2014; the entire contents of which are incorporated herein by reference.

FIELD

Embodiments described herein relate generally to a medical diagnostic imaging apparatus, an image processing apparatus, and an image processing method.

BACKGROUND

Conventionally, to evaluate the cardiac function objectively and quantitatively, techniques have been available that obtain a motion index regarding, for example, a displacement or a strain of tissue in the heart. For example, an ultrasonic diagnostic apparatus collects three-dimensional ultrasonic image data of the heart in a time series, performs pattern matching of a local region on ultrasonic images, performs tracking of the local region, and thereby estimates the motion index of the heart. The ultrasonic diagnostic apparatus then generates an image of the heart (or a cardiac ventricle, a cardiac atrium, or another part) included in a region of interest defined by an operator by rendering processing, and displays the estimated motion index on a rendering image with color coding applied thereto, for example.

BRIEF DESCRIPTION OF THE DRAWINGS

FIG. 5 is a flowchart for explaining the processing of the ultrasonic diagnostic apparatus in the first embodiment;

FIG. 7 is a block diagram illustrating an example of the configuration of an image processing system according to other embodiments.

DETAILED DESCRIPTION

A medical diagnostic imaging apparatus according to an embodiment includes control circuitry. The control circuitry obtains three-dimensional medical image data obtained by acquiring an area of an object. The control circuitry defines a setting region on the three-dimensional medical image data. The control circuitry divides the setting region into a region of interest and a region other than the region of interest by at least a single boundary position. The control circuitry generates, from the three-dimensional medical image data, an image in which the region of interest and the region other than the region of interest are distinguished from each other. The control circuitry calculates information about at least one of the volume of and a motion index of the region of interest. The control circuitry displays the calculated information for the region of interest in the image.

With reference to the accompanying drawings, the following describes a medical diagnostic imaging apparatus, an image processing apparatus, and an image processing method according to embodiments.

In the following description, situations are explained in which the embodiments are applied to an ultrasonic diagnostic apparatus as one example of the medical diagnostic imaging apparatus. The embodiments, however, are not limited to this. For example, the embodiments may be applied to an X-ray diagnostic apparatus, an X-ray computed tomography (CT) apparatus, a magnetic resonance imaging (MRI) apparatus, a single photon emission computed tomography (SPECT) apparatus, a positron emission tomography (PET) apparatus, a SPECT-CT apparatus in which a SPECT apparatus and an X-ray CT apparatus are integrally combined, a PET-CT apparatus in which a PET apparatus and an X-ray CT apparatus are integrally combined, a PET-MRI apparatus in which a PET apparatus and an MRI apparatus are integrally combined, or a group of apparatuses that includes a plurality of the foregoing apparatuses.

First Embodiment

Figure 1:
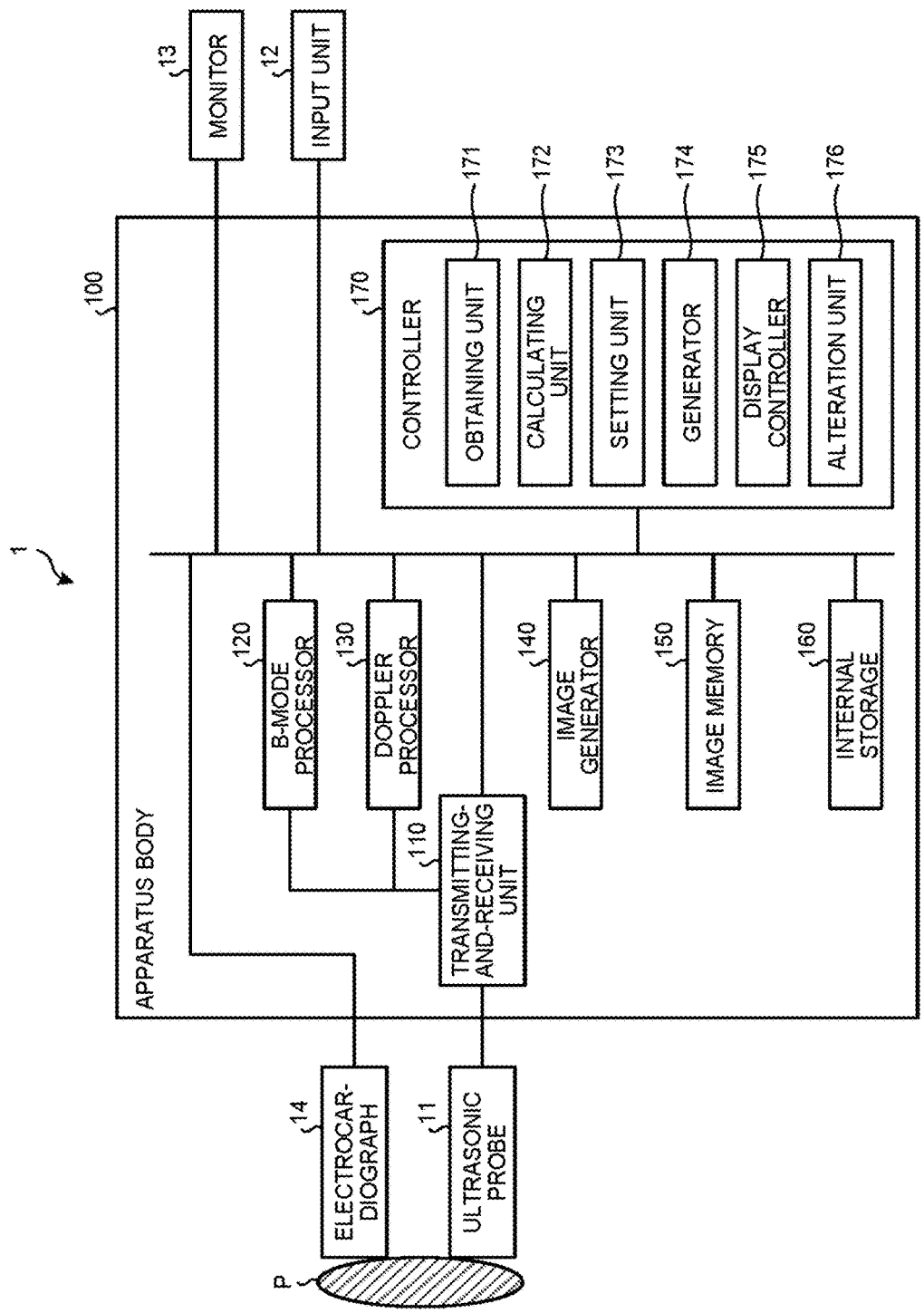
FIG. 1 is a block diagram illustrating an example of the configuration of an ultrasonic diagnostic apparatus according to a first embodiment.

FIG. 1 is a block diagram illustrating an example of the configuration of an ultrasonic diagnostic apparatus according to a first embodiment. As illustrated in FIG. 1, an ultrasonic diagnostic apparatus 1 in the first embodiment includes an ultrasonic probe 11, an input unit 12, a monitor 13, an electrocardiograph 14, and an apparatus body 100.

The ultrasonic probe 11 includes a plurality of piezoelectric transducer elements, and these piezoelectric transducer elements generate ultrasonic waves based on drive signals supplied from a transmitting-and-receiving unit 110 of the apparatus body 100 which will be described later. The ultrasonic probe 11 receives reflected waves from an object P and converts them into electrical signals. The ultrasonic probe 11 further includes, for example, a matching layer that is provided on the piezoelectric transducer elements, a backing material that prevents ultrasonic waves from propagating toward the rear from the piezoelectric transducer elements. The ultrasonic probe 11 is detachably connected to the apparatus body 100.

When ultrasonic waves are transmitted to the object P from the ultrasonic probe 11, the transmitted ultrasonic waves are successively reflected by a surface where acoustic impedance is discontinuous in the body tissue of the object P, and are received by the piezoelectric transducer elements of the ultrasonic probe 11 as reflected wave signals. The amplitude of the reflected wave signal received is dependent on the difference in acoustic impedance at the discontinuous surface by which the ultrasonic waves are reflected. When a transmitted ultrasonic pulse is reflected by, for example, the surface of blood flow or the myocardium in motion, the reflected wave signal undergoes frequency deviation that is dependent on the velocity component of a moving body with respect to the transmitting direction of the ultrasonic waves by the Doppler effect.

For example, in the first embodiment, for three-dimensional scanning of the object P, a mechanical 4D probe or a 2D array probe is connected to the apparatus body 100 as the ultrasonic probe 11. The mechanical 4D probe is capable of performing two-dimensional scans by using a plurality of piezoelectric transducer elements arrayed in a single row as in a 1D array probe, and is also capable of performing three-dimensional scans by swinging the piezoelectric transducer elements at a given angle (swing angle). The 2D array probe is capable of performing three-dimensional scans by a plurality of piezoelectric transducer elements disposed in a matrix, and is also capable of performing two-dimensional scans by focusing and transmitting ultrasonic waves.

The input unit 12 includes a mouse, a keyboard, buttons, panel switches, a touch command screen, a foot switch, a trackball, a joystick, and other devices, receives various setting requests from an operator of the ultrasonic diagnostic apparatus 1, and transfers the received various setting requests to the apparatus body 100.

The monitor 13 displays a graphical user interface (GUI) for the operator of the ultrasonic diagnostic apparatus 1 to input various setting requests by using the input unit 12, and displays ultrasonic image data generated in the apparatus body 100 and other data.

The electrocardiograph 14 acquires electrocardiogram (ECG) of the object P as a biosignal of the object P that is ultrasonically scanned. The electrocardiograph 14 transmits the acquired ECG to the apparatus body 100.

The apparatus body 100 is a device that generates ultrasonic image data based on the reflected wave signals received by the ultrasonic probe 11. The apparatus body 100 illustrated in FIG. 1 is a device capable of generating two-dimensional ultrasonic image data based on two-dimensional reflected wave data received by the ultrasonic probe 11. Furthermore, the apparatus body 100 illustrated in FIG. 1 is a device capable of generating three-dimensional ultrasonic image data based on three-dimensional reflected wave data received by the ultrasonic probe 11. The three-dimensional ultrasonic image data is one example of "three-dimensional medical image data" or "volume data."

The apparatus body 100 includes, as illustrated in FIG. 1, the transmitting-and-receiving unit 110, a B-mode processor 120, a Doppler processor 130, an image generator 140, an image memory 150, internal storage 160, and a controller 170.

The transmitting-and-receiving unit 110 includes a pulse generator, a transmission delay unit, a pulser, and other units, and supplies drive signals to the ultrasonic probe 11. The pulse generator repeatedly generates rate pulses to form ultrasonic waves at a given rate frequency. The transmission delay unit assigns, to each of the rate pulses generated by the pulse generator, a delay time that is necessary for each of the piezoelectric transducer elements to focus the ultrasonic waves generated by the ultrasonic probe 11 into a beam shape and to determine the transmission directivity. The pulser applies the drive signals (drive pulses) to the ultrasonic probe 11 at the timing based on the rate pulses. That is, the transmission delay unit varies the delay times assigned to the respective rate pulses, and thereby adjusts, into any desired direction, the transmission direction of the ultrasonic waves transmitted from the plane of the piezoelectric transducer elements.

The transmitting-and-receiving unit 110 has a function capable of instantly changing, for example, transmission frequencies or transmission drive voltages in order to execute a given scan sequence, based on instructions of the controller 170 which will be described later. In particular, changing transmission drive voltages is implemented by an oscillator circuit of a linear amplifier type capable of instantly switching values thereof or by a mechanism that electrically switches a plurality of power supply units.

The transmitting-and-receiving unit 110 further includes a pre-amplifier, an analog-to-digital (A/D) converter, a reception delay unit, an adder, and other units, and performs a variety of processing on the reflected wave signals received by the ultrasonic probe 11 and thereby generates reflected wave data. The pre-amplifier amplifies the reflected wave signal for each channel. The A/D converter performs A/D conversion on the amplified reflected wave signal. The reception delay unit assigns delay times necessary to determine the reception directivity. The adder performs addition processing on the reflected wave signal processed by the reception delay unit and generates the reflected wave data. By the addition processing of the adder, the reflection component of the reflected wave signal from a direction corresponding to the reception directivity is emphasized. By the reception directivity and the transmission directivity, an overall beam of ultrasonic transmission and reception is formed.

When scanning a two-dimensional region of the object P, the transmitting-and-receiving unit 110 causes the ultrasonic probe 11 to transmit an ultrasonic beam in two-dimensional directions. The transmitting-and-receiving unit 110 then generates two-dimensional reflected wave data from reflected wave signals received by the ultrasonic probe 11. When scanning a three-dimensional region of the object P, the transmitting-and-receiving unit 110 causes the ultrasonic probe 11 to transmit an ultrasonic beam in three-dimensional directions. The transmitting-and-receiving unit 110 then generates three-dimensional reflected wave data from reflected wave signals received by the ultrasonic probe 11.

The form of the output signal from the transmitting-and-receiving unit 110 is selectable from various forms such as a case of a signal referred to as a radio frequency (RF) signal in which phase information is included and a case of amplitude information after envelope detection processing.

The B-mode processor 120 receives the reflected wave data from the transmitting-and-receiving unit 110, performs the processing of logarithmic amplification, envelope detection, and other processing, and generates data in which the signal intensity is expressed by the brightness of luminance (B-mode data).

The Doppler processor 130 performs frequency analysis on velocity information from the reflected wave data received from the transmitting-and-receiving unit 110, extracts a blood flow, tissue, or an echo component of a contrast agent by the Doppler effect, and generates data (Doppler data) in which moving body information such as the velocity, the dispersion, and the power has been extracted at multi-points.

The B-mode processor 120 and the Doppler processor 130 in the first embodiment are capable of performing processing on both the two-dimensional reflected wave data and the three-dimensional reflected wave data. That is, the B-mode processor 120 generates two-dimensional B-mode data from the two-dimensional reflected wave data and generates three-dimensional B-mode data from the three-dimensional reflected wave data. The Doppler processor 130 generates two-dimensional Doppler data from the two-dimensional reflected wave data and generates three-dimensional Doppler data from the three-dimensional reflected wave data.

The image generator 140 generates ultrasonic image data from the data generated by the B-mode processor 120 and the Doppler processor 130. That is, the image generator 140 generates two-dimensional B-mode image data that represents the intensity of reflected waves in luminance from the two-dimensional B-mode data generated by the B-mode processor 120. The image generator 140 further generates two-dimensional Doppler image data that represents the moving body information from the two-dimensional Doppler data generated by the Doppler processor 130. The two-dimensional Doppler image data is velocity image data, dispersion image data, power image data, or image data of the combination of the foregoing. The image generator 140 is also capable of generating Doppler waveforms in which the velocity information on blood flow and tissue is plotted in a time series from the Doppler data generated by the Doppler processor 130.

The image generator 140, in general, converts (scan-converts) the scanning-line signal sequences of ultrasonic scans into scanning-line signal sequences of a video format typified by television and the like, and generates ultrasonic image data for display. Specifically, the image generator 140 performs coordinate conversion depending on the scanning form of ultrasonic waves by the ultrasonic probe 11 and thereby generates the ultrasonic image data for display. The image generator 140, by using a plurality of image frames after scan conversion, further performs image processing (smoothing processing) to regenerate an image with an average luminance value and image processing (edge enhancement processing) that applies a differential filter within an image, as a variety of image processing other than the scan conversion, for example. The image generator 140 combines character information of various parameters, scales, body marks, and other information with the ultrasonic image data.

That is, the B-mode data and the Doppler data are ultrasonic image data before scan conversion processing, and the data that the image generator 140 generates is the ultrasonic image data for display after scan conversion processing. The B-mode data and the Doppler data are also referred to as raw data.

Furthermore, the image generator 140 performs coordinate conversion on the three-dimensional B-mode data generated by the B-mode processor 120 and thereby generates three-dimensional B-mode image data. The image generator 140 further performs coordinate conversion on the three-dimensional Doppler data generated by the Doppler processor 130 and thereby generates three-dimensional Doppler image data. That is, the image generator 140 makes "three-dimensional B-mode image data and three-dimensional Doppler image data" into "three-dimensional ultrasonic image data (volume data)."

Moreover, the image generator 140 performs rendering processing on volume data to generate a variety of two-dimensional image data to display the volume data on the monitor 13. The rendering processing to be performed by the image generator 140 includes the processing of generating multi-planar reconstruction (MPR) image data from the volume data by performing MPR. Furthermore, the rendering processing to be performed by the image generator 140 includes the processing of performing "curved MPR" on the volume data and the processing of performing "maximum intensity projection" on the volume data. The rendering processing to be performed by the image generator 140 further includes volume rendering (VR) processing and surface rendering (SR) processing.

The image memory 150 is a memory that stores therein the image data for display generated by the image generator 140. The image memory 150 can also store therein the data generated by the B-mode processor 120 and the Doppler processor 130. The B-mode data and the Doppler data stored in the image memory 150 can be called up by the operator after diagnosis, and are made into the ultrasonic image data for display via the image generator 140, for example.

The image generator 140 stores, in the image memory 150, ultrasonic image data and the time of an ultrasonic scan performed to generate the ultrasonic image data, in association with the ECG transmitted from the electrocardiograph 14. The controller 170 which will be described later can acquire a cardiac phase at the time of the ultrasonic scan performed to generate the ultrasonic image data by referring to the data stored in the image memory 150.

The internal storage 160 stores therein control programs to perform ultrasonic transmission and reception, image processing, and display processing, and stores a variety of data such as diagnostic information (for example, patient IDs and doctor's findings), diagnosis protocols, and various body marks. The internal storage 160 is used also for the archive of the image data stored in the image memory 150 as necessary. The data stored in the internal storage 160 can be transferred to an external device via an interface not depicted. The external device includes a high-performance work station for image processing, a personal computer (PC) used by a doctor who performs image diagnosis, a storage medium such as a CD and a DVD, and a printer, for example.

The controller 170 controls the overall processing of the ultrasonic diagnostic apparatus 1. Specifically, based on the various setting requests received from the operator via the input unit 12, and on various control programs and a variety of data read in from the internal storage 160, the controller 170 controls the processing of the transmitting-and-receiving unit 110, the B-mode processor 120, the Doppler processor 130, and the image generator 140. Furthermore, the controller 170 performs control so as to display the ultrasonic image data for display stored in the image memory 150 and the internal storage 160 on the monitor 13.

Furthermore, the controller 170 provides a motion index (motion information) of tissue that periodically moves. For example, the controller 170 obtains the ultrasonic image data of the heart stored in the image memory 150, performs wall motion tracking (WMT) of the heart by image processing, and thereby calculates a motion index of a myocardium. The controller 170 then stores the generated motion index in the image memory 150 or the internal storage 160. The processing of the controller 170 to calculate the motion index will be described later.

In the conventional techniques, there are cases in which it is difficult to comprehend a situation around a boundary of a region of interest defined on a three-dimensional image. For example, when a right ventricle (RV) is three-dimensionally displayed as a region of interest, an inflow portion through which blood flows into the RV is left out with a tricuspid valve as a boundary, an outflow portion through which the blood flows out from the RV is left out with a pulmonary valve as a boundary, and thus only the RV is displayed. In such a case, it is difficult to comprehend the situation in the peripheries of the respective boundaries of the tricuspid valve and the pulmonary valve.

It is considered useful if the boundary of the region of interest can be altered when it is difficult to comprehend the situation around the boundary of the region of interest or when the position of the boundary is hard to recognize depending on image quality. In the conventional technologies, however, the boundary position cannot be altered in a state that the analysis result is being displayed, and thus the trouble of returning to the setting of inputting the boundary position is needed.

Consequently, the ultrasonic diagnostic apparatus 1 in the first embodiment is provided with the following configuration to facilitate the comprehension of a situation around the boundary of a region of interest defined on a three-dimensional image.

The controller 170 in the first embodiment includes an obtaining unit 171, a calculating unit 172, a setting unit 173, a generator 174, a display controller 175, and an alteration unit 176.

In the following description, a situation will be explained in which the controller 170 performs the WMT of the heart and calculates the motion index of the myocardium. The first embodiment, however, is not limited to this. For example, what the controller 170 can calculate is not limited to the WMT, and further includes the information concerning the volume of myocardium, and the volume inside the cardiac cavities.

The obtaining unit 171 obtains three-dimensional medical image data obtained by acquiring an area of an object including a plurality of regions of interest that are connected. In the first embodiment, the regions of interest included in the area of the object include the RV, a right-ventricular inflow portion that lets blood flow into the RV, and a right-ventricular outflow portion that lets blood flow out from the RV. For example, the obtaining unit 171 obtains, for at least one heartbeat, three-dimensional medical image data obtained by photographing at least a part of the heart as the area. In other words, the obtaining unit 171 as obtaining circuitry obtains the three-dimensional medical image data obtained by photographing the area of the object.

For example, with a sector probe, the operator performs three-dimensional scans on a region around the RV (the RV, the right-ventricular inflow portion, and the right-ventricular outflow portion) of the object P, and photographs moving image data of three-dimensional ultrasonic image data in which a myocardium is portrayed. This moving image data is a group of ultrasonic image data including the ultrasonic image data collected by B-mode for each time phase, for example. The "time phase" indicates any of one time point (timing) in periodical motion of the heart and is also referred to as "cardiac phase."

The image generator 140 then generates moving image data of the region around the RV, and stores the generated moving image data in the image memory 150. The operator then defines a section for one heartbeat from an R-wave to a subsequent R-wave in the ECG as the section of processing target, for example. The first embodiment is applicable even when the section used as a processing target is defined as a section for two heartbeats and as a section for three heartbeats.

The obtaining unit 171 then obtains a group of ultrasonic image data from the image memory 150, for example. This group of ultrasonic image data includes three-dimensional ultrasonic image data (volume data) of a plurality of frames included in the section for one heartbeat defined by the operator.

In the first embodiment, a situation of obtaining volume data extending over a plurality of time phases has been described to explain an application example to a typical speckle tracking method. The first embodiment, however, is not limited to this. For example, the obtaining unit 171 may obtain the volume data corresponding to a single time phase. Consequently, the obtaining unit 171 may obtain the volume data of a single time phase corresponding to end-diastole or end-systole, for example.

In the first embodiment, a situation will be explained in which three-dimensional ultrasonic image data obtained by photographing the RV is obtained by the obtaining unit 171 and is used in the following processing. The first embodiment, however, is not limited to this. For example, the three-dimensional ultrasonic image data that the obtaining unit 171 obtains may be data obtained by photographing a left ventricle, or may be data obtained by photographing the heart as a whole or an area other than the heart.

In the first embodiment, a situation will be explained in which three-dimensional ultrasonic image data generated by the transmission and reception of ultrasonic waves is used as the three-dimensional medical image data. The first embodiment, however, is not limited to this. For example, the three-dimensional medical image data may be three-dimensional medical image data generated by a medical diagnostic imaging apparatus different from the ultrasonic diagnostic apparatus such as an X-ray diagnostic apparatus, an X-ray CT apparatus, an MRI apparatus, a SPECT apparatus, a PET apparatus, a SPECT-CT apparatus in which a SPECT apparatus and a CT apparatus are integrally combined, a PET-CT apparatus in which a PET apparatus and a CT apparatus are integrally combined, a PET-MRI apparatus in which a PET apparatus and an MRI apparatus are integrally combined, or a group of apparatuses including a plurality of the foregoing apparatuses.

The calculating unit 172 calculates information about at least one of the volume of and the motion index of a given region from the three-dimensional medical image data. For example, the calculating unit 172 calculates the information about at least one of the volume and the motion index, by the processing including pattern matching between pieces of three-dimensional medical image data included in the three-dimensional medical data for at least one heartbeat obtained by the obtaining unit 171.

The calculating unit 172 first defines a plurality of regions of interest on a group of three-dimensional medical image data. The regions of interest defined in the first embodiment include the RV, the right-ventricular inflow portion, and the right-ventricular outflow portion, and because these regions are connected with one another, it is substantially equivalent to defining a single region of interest. In other words, the calculating unit 172 as region-setting circuitry defines a setting region on the three-dimensional medical image data. Specifically, these regions are defined by, for example, segmentation of boundaries based on boundary detection means concerning the RV and the connected tissue as a whole or means for manually setting boundary positions. The right-ventricular inflow portion is a tubular structure including the tricuspid valve and the right-ventricular outflow portion is a tubular structure including the pulmonary valve.

Subsequently, the calculating unit 172 defines identification information for identifying respective positions for a plurality of positions representing the outline of the RV in the three-dimensional medical image data on which a plurality of regions of interest have been defined. For example, the calculating unit 172 defines a plurality of tracking points, to which the addresses are assigned, at positions corresponding to the contours (surface) of the RV in at least one piece of ultrasonic image data included in a group of ultrasonic image data. The tracking point is a point that is tracked over time to calculate a motion index of a local region, and is a composition point that constitutes the contours of the local region. The address is a number assigned for identifying each of the tracking points, and is defined based on the position of the respective tracking points of, for example, the endocardium. The addresses are not limited to numbers, and only need to be identification information, such as characters or symbols, which allows identification of the positions of the respective tracking points.

While a situation in which, as one example, the following processing is performed on the endocardium of the RV is described, the first embodiment is not limited to this. For example, the following processing is performed on an area not limited to the endocardium, and may be performed on the epicardium or on an intermediate layer between the endocardium and epicardium. In the calculating unit 172, the following processing is performed on a region not limited to the RV, and may be performed on any given region such as a left ventricle, a left cardiac atrium, a right cardiac atrium, or the heart as a whole, for example. In the first embodiment, the calculating unit 172 defines a plurality of composition points constituting the contours at positions corresponding to the initial contours of the heart in accordance with the information manually defined by the operator.

For example, the operator specifies any desired cardiac phase for a group of volume data obtained by the obtaining unit 171. The desired cardiac phase specified here is any desired frame out of the frames included in the section for one heartbeat, and is an end-diastolic phase (the first R-wave phase), for example. When the desired cardiac phase is then specified by the operator, the calculating unit 172 inputs the outline of the myocardium region of a first area for performing the inflow of blood to the RV by using a cross-section along the axis of the first area, and defines a three-dimensional shape that approximates the first area by interpolation processing, on the volume data of the heart at the specified cardiac phase.

The calculating unit 172 then inputs the outline of the myocardium region of a second area for performing the outflow of blood from the RV on a cross-sectional image along the axis of the second area, and defines a three-dimensional shape that approximates the second area by interpolation processing, on the volume data corresponding to the above-described cardiac phase.

Moreover, the calculating unit 172 defines the three-dimensional myocardium shape of the ventricle including the first area and the second area on the volume data by using the approximated three-dimensional shape of the first area and the approximated three-dimensional shape of the second area. As a result, as illustrated in FIG. 2, a three-dimensional myocardium shape VE of the ventricle including the three-dimensional shape of a first area VI and the three-dimensional shape of a second area VO is defined (or extracted), for example.

Figure 2:
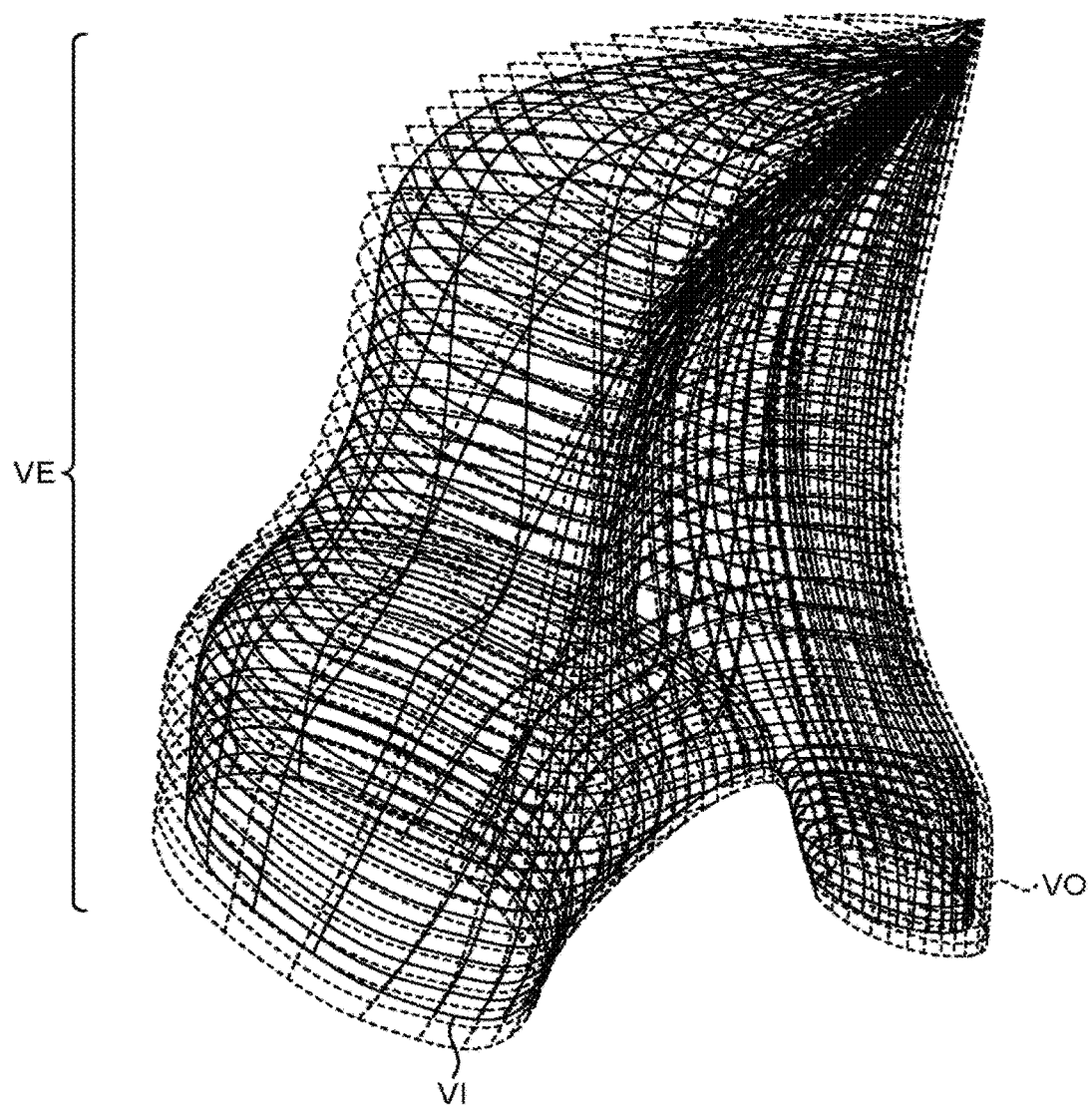
FIG. 2 is a diagram for explaining composition points defined by a calculating unit in the first embodiment.

At this time, the calculating unit 172 assigns respective addresses to a plurality of composition points (corresponding to the position of each intersection of respective meshes in the mesh display in FIG. 2) constituting the initial contours of the endocardium in three dimension. The calculating unit 172 defines the position of each composition point of the endocardium as $P\_endo(t,h,d)$, for example. The variable t represents a frame (cardiac phase) that is included in the section for one heartbeat, the variable h represents an address number in a longitudinal direction (height), and the variable d represents an address number in a circumferential direction (orientation). Because the initial cross-section is defined here by using the first R-wave phase, t=0. FIG. 2 is a diagram for explaining the composition points defined by the calculating unit 172 in the first embodiment.

The calculating unit 172 defines an end portion of the first area (on the tricuspid valve side), for example, as the reference position in the circumferential direction, and defines the value of d of the composition point of that position as zero. That is, the position of the composition point located at this reference position is expressed as $P\_endo(0,h,0)$. The calculating unit 172 then sets the address numbers to the composition points that lie in the circumferential direction from the composition point at the reference position in sequence as d=1, 2, 3, and so on. The calculating unit 172 further defines the position of the annular contours farthest from a ventricular apex portion out of the three-dimensional initial contours as the reference position in the longitudinal direction, and defines the value of h of the composition point at that position as zero. That is, the position of the composition point located at this reference position is expressed as $P\_endo(0,0,d)$. The calculating unit 172 then sets the address numbers to the composition points that lie in the ventricular apex direction from the composition point at the reference position in sequence as h=1, 2, 3, and so on.

The calculating unit 172 then performs tracking of the positions of a plurality of composition points in a plurality of pieces of ultrasonic image data included in the group of ultrasonic image data by performing processing that includes pattern matching by using the ultrasonic image data at the initial time phase in which the composition points have been defined and the ultrasonic image data at a subsequent time phase.

For example, when a plurality of composition points are defined at positions corresponding to the initial contours in the volume data at the frame t=0 included in a group of volume data, the calculating unit 172 performs tracking of the positions of the respective composition points at other frames t by the processing including pattern matching. Specifically, the calculating unit 172 repeatedly performs the pattern matching between the volume data at the frame in which a plurality of composition points have already been defined and the volume data at the frame adjacent to that frame. That is, with the respective composition points $P\_endo(0,h,d)$ of the endocardium in the volume data at t=0 as the point of origin, the calculating unit 172 performs the tracking of the positions of the respective composition points $P\_endo(t,h,d)$ in the volume data of the respective frames at t=1, 2, 3, and so on. As a result, the calculating unit 172 obtains coordinate information on the respective composition points constituting the endocardium at the respective frames included in the section for one heartbeat.

Using the positions of a plurality of composition points in a plurality of pieces of ultrasonic image data included in each group of ultrasonic image data, the calculating unit 172 then calculates the motion index representing the motions of tissue for the respective pieces of ultrasonic image data.

The representative examples of the motion index that is calculated by the calculating unit 172 include: a regional myocardial displacement (mm) of the respective composition points for each one frame; a regional myocardial strain (%) that is a change rate of a distance between two points; and a regional myocardial velocity (cm/s) and a regional myocardial strain rate (l/s) that are the respective temporal differential of the foregoing. The motion index, however, is not limited to these parameters, and only needs to be a parameter that can be calculated by using the coordinate information on a plurality of composition points in the respective frames. For example, each of these motion indices may be separated into components. In the case of the RV, a longitudinal strain (LS) obtained by separating out a longitudinal direction component and circumferential strain (CS) obtained by separating out a circumferential direction component are used, for example. These indices are calculated by the speckle tracking method in two dimension using two-dimensional images (a long axis view and a short axis view) of the RV. In the three-dimensional speckle tracking method, a local area change ratio (AC) may be defined. Because the AC requires no component separation, the AC can yield a stable analysis even in a complicated shape as with the RV.

Available as the motion index frequently used in clinical practices for the functional evaluation of the RV is a tricuspid annular plane systolic excursion (TAPSE) that is measured with the M mode. Because the M mode is a one-dimensional analysis, the TAPSE allows observation of a displacement component toward the direction of the ultrasonic probe on a part near the tricuspid annulus. In contrast, in the three-dimensional speckle tracking method, the information about the displacement covering the entire region of the RV is obtained. As for the direction of displacement in this case, the displacement components in the longitudinal direction with reference to the region of interest (RV) and in a wall-thickness (radial) direction are detectable. As an index that is hard to be influenced by a complicated shape of the RV, a moving distance D (D=sqrt((Px(n)−Px(n0))^2+ ((Py(n)−Py(n0))^2+((Pz(n)−Pz(n0))^2)) in which no separation into directional components is performed may be used. Note that the (Px(n),Py(n),Pz(n)) represents the position of a tracking point P, the variable n represents a time phase, and the variable n0 represents the reference time phase.

Values of the motion index calculated by the calculating unit 172 are assigned to the respective composition points (tracking points) used for the calculation. Specifically, values of the motion index calculated from the respective composition points of the endocardium are defined as V_endo(t,h,d). The calculating unit 172 then stores the calculated values of the motion index in the image memory 150 for each group of volume data.

The calculating unit 172 further calculates volume as an index of a pump function of the heart. For example, the calculating unit 172 calculates the volume of the region of interest including the RV. The region, the volume of which is calculated by the calculating unit 172, can be altered as appropriate.

As in the foregoing, the calculating unit 172 calculates the information including at least one of the volume of and the motion index of the heart on a group of ultrasonic image data. In other words, the calculating unit 172 as calculating circuitry calculates the information about at least one of the volume of and the motion index concerning the region of interest.

The setting unit 173 defines, in a region in which a plurality of regions of interest are connected, a first region of interest and a second region of interest other than the first region of interest, by at least a single boundary position defined on the regions of interest. In other words, the setting unit 173 as a boundary-setting unit divides a setting region into a region of interest and regions other than that by at least a single boundary position.

For example, the setting unit 173 receives, on a plurality of regions of interest defined by the calculating unit 172, the input that specifies a boundary position from the operator. The setting unit 173 then defines, as the first region of interest, the region included in the boundary position specified by the received input. The setting unit 173 defines the boundary position so as for the boundary position to pass any of the composition points defined by the calculating unit 172. As a result, the setting unit 173 divides the regions of interest into the first region of interest and the second region of interest other than the first region of interest.

Specifically, the setting unit 173 receives, on a plurality of regions of interest including the RV, the right-ventricular inflow portion (first area), and the right-ventricular outflow portion (second area), the input that specifies an arbitrary annular position in the right-ventricular inflow portion and an arbitrary annular position in the right-ventricular outflow portion, as respective boundary positions. The setting unit 173 then defines, as the first region of interest, the region including the RV surrounded by these boundary positions, and defines the tubular structures on the outside of these boundary positions as the second region of interest.

While the situation in which the setting unit 173 defines the first region of interest by the boundary positions manually set by the operator has been described, the embodiment is not limited to this. For example, the boundary positions may be preset, and the setting unit 173 may define the first region of interest by using the preset boundary positions. These preset boundary positions are defined by the diameter of a tubular structure or by the position or the like of a structure (for example, a tricuspid valve or a pulmonary valve) recognized by pattern matching, for example. The above-described example is merely an example, and the first region of interest may be the left ventricle and the second region of interest may be other than the left cardiac atrium and a tubular structure, for example.

The generator 174 generates, from the three-dimensional medical image data, an image that includes a plurality of regions of interest and in which the first region of interest and the second region of interest are distinguished from each other. For example, the generator 174 performs SR processing on three-dimensional medical image data in which a plurality of regions of interest are divided into the first region of interest and the second region of interest, and generates an SR image. In other words, the generator 174 as generating circuitry generates, from the three-dimensional medical image data, an image in which the region of interest and the regions other than that are distinguished.

For example, the generator 174 performs SR processing on volume data in which the region of the RV including the tricuspid valve and the pulmonary valve is defined as the first region of interest and the regions outside of that are defined as the second region of interest, and generates an SR image. The generator 174 displays the first region of interest with given color codes and displays the second region of interest with wire frames. Consequently, when viewing a three-dimensional display of the SR images and the like, a user is able to check the first region of interest that is a valid region including the RV, the tricuspid valve, and the pulmonary valve while distinguishing the first region of interest from the regions outside of that (second region of interest).

While the situation in which the generator 174 displays the first region of interest with color codes and displays the second region of interest with wire frames has been described, the first embodiment is not limited to this. For example, the generator 174 may display the first region of interest and the second region of interest with respective color codes different from each other. In this case, the generator 174 displays the first region of interest with a color map based on the motion index and displays the second region of interest by a color not present in the color map (such as gray).

The display controller 175 displays, on the image, the information about the first region of interest out of the information calculated by the calculating unit 172. For example, the display controller 175 converts the information including at least one of the volume and the motion index calculated by the calculating unit 172 into color codes, and performs the mapping thereof on the image generated by the generator 174. For example, the display controller 175 displays this image on the monitor 13 as the moving image data for one heartbeat. As for the mapping method of motion index distribution, a three-dimensional display method that performs surface rendering of the endocardium surface is suitable.

Figure 3A:
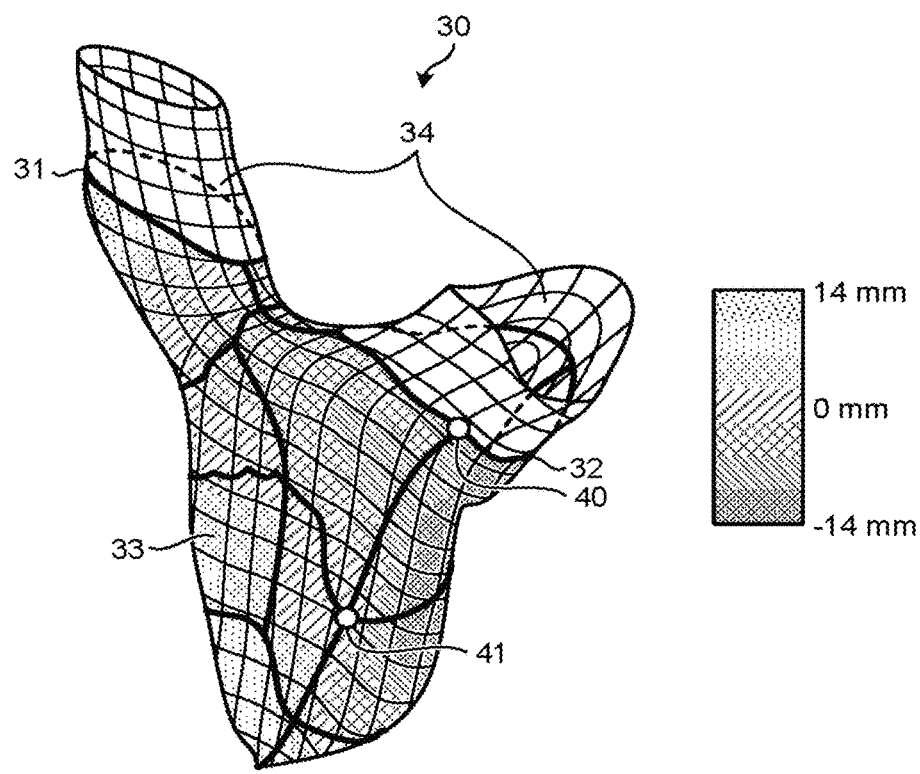
FIGS. 3A and 3B are diagrams illustrating examples of a display screen displayed by a display controller in the first embodiment.
Figure 3B:
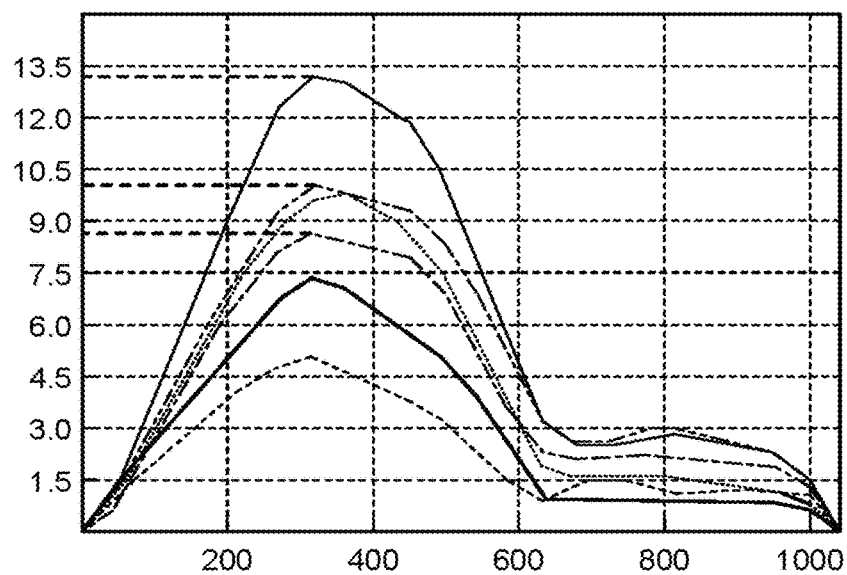

FIGS. 3A and 3B are diagrams illustrating examples of a display screen displayed by the display controller 175 in the first embodiment. FIG. 3A is one example of a rendering image displayed by the display controller 175, and FIG. 3B is one example of time-changing curves displayed by the display controller 175.

In the example illustrated in FIG. 3A, the display controller 175 displays a rendering image of a connected region 30 in which three regions of interest including the RV, the right-ventricular inflow portion, and the right-ventricular outflow portion are connected. The connected region 30 is divided into a first region of interest 33 and a second region of interest 34, by an annular boundary position 31 defined in the right-ventricular outflow portion and an annular boundary position 32 defined in the right-ventricular inflow portion. The first region of interest 33 is divided into 14 regions. The display controller 175 displays the above-described moving distance D on this first region of interest 33 with color coding applied thereto. The second region of interest 34 is displayed by wire frames by the generator 174.

In the example illustrated in FIG. 3B, the display controller 175 displays the time-changing curves of the moving distance D by a graphic chart. Out of the 14 divided regions, six regions are selected and displayed here as the graphic chart. That is, the display controller 175 displays the average values of the moving distances D of the composition points included in the respective six regions as six time-changing curves. This value is widely used for the purposes of mainly the evaluation of degree of peak value and the evaluation of timing of the peak. Furthermore, regions the values of motion index of the respective divided regions among all of the regions can be used as an index of a global myocardial function for generating a pump function of the cardiac cavities.

While the situation in which the moving distance D is selected as the information to be displayed has been exemplified in the example in FIGS. 3A and 3B, this example is not limiting. For example, the display controller 175 may display other values calculated by the calculating unit 172. While the situation in which the RV is divided into 14 regions has been exemplified in the example in FIG. 3A, this example is not limiting. For example, it may be divided into any desired number of regions or may not be divided at all.

As in the foregoing, the display controller 175 displays, on the image, the information about the first region of interest out of the information calculated by the calculating unit 172.

The alteration unit 176 receives instructions from the operator and alters a boundary position in response to the instructions. For example, the alteration unit 176 alters the boundary position so as to pass any of a plurality of positions.

Figure 4A:
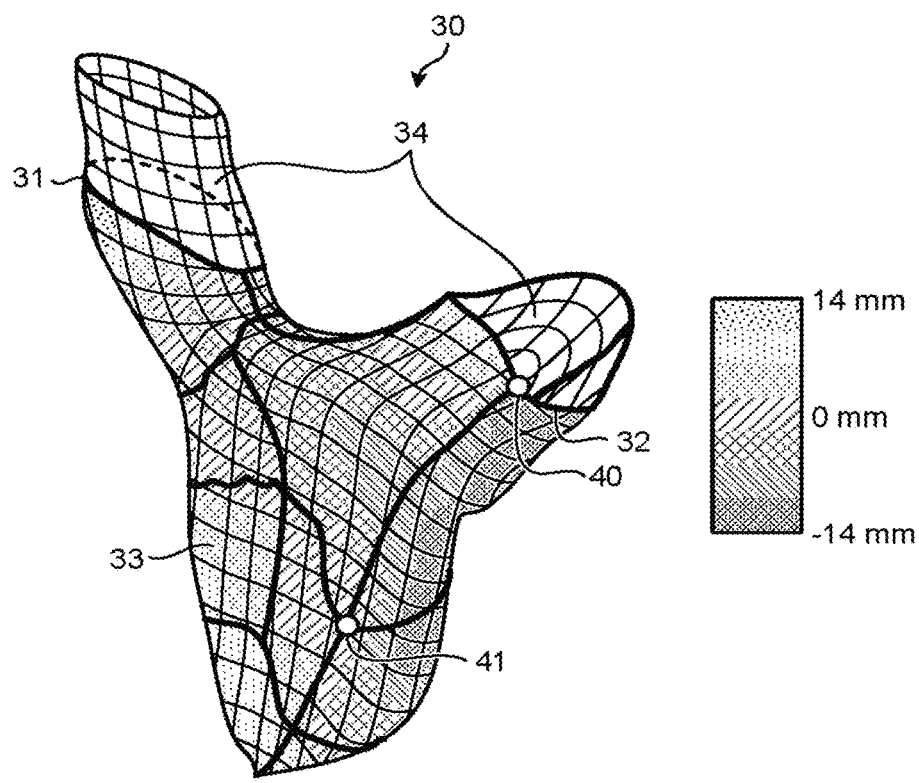
FIGS. 4A and 4B are diagrams for explaining the processing of an alteration unit in the first embodiment.
Figure 4B:
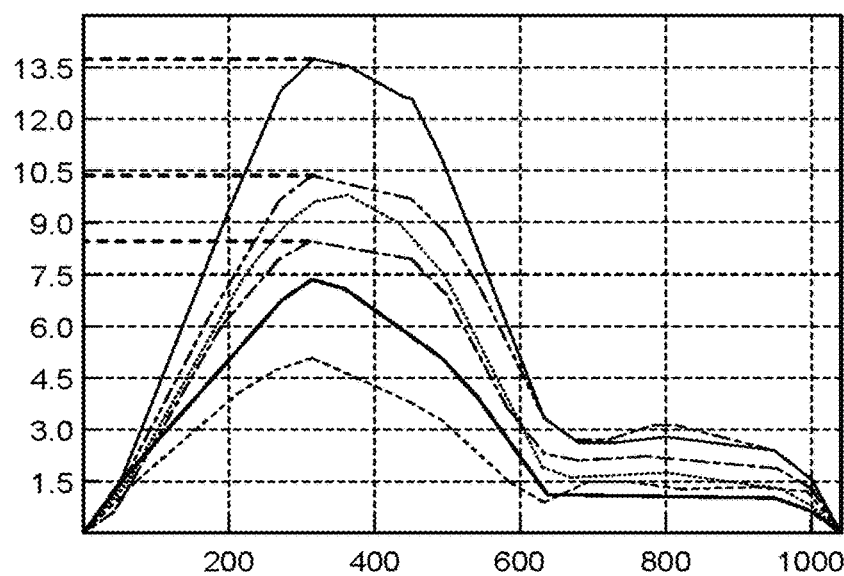

FIGS. 4A and 4B are diagrams for explaining the processing of the alteration unit 176 in the first embodiment. FIG. 4A is one example of the rendering image after having altered an annular level of the boundary position 32 in FIG. 3A, and FIG. 4B is one example of the time-changing curves of the moving distance D corresponding to FIG. 4A. That is, FIGS. 3A to 4B illustrate the situation in which the annular level of the boundary position 32 is altered from a valve ring (tricuspid valve) position (FIG. 3A and FIG. 3B) of the right-ventricular inflow portion to an end portion (FIG. 4A and FIG. 4B) of the right-ventricular inflow portion. The broken line portions indicated in FIGS. 3B and 4B correspond to peak values of the moving distance D in three regions corresponding to a basal area.

The alteration unit 176 first receives input that specifies a boundary position to be an object of alteration. For example, in the example in FIG. 3A, the boundary position 31 and the boundary position 32 are displayed such that they can be specified as an object of alteration. For example, the "I" key on a keyboard is assigned to the boundary position 32 and the "O" key on the keyboard is assigned to the boundary position 31. In this case, for example, when the "I" key on the keyboard is pressed down, the alteration unit 176 receives that as an indication that the boundary position 32 has been specified as an object of alteration. The alteration unit 176 may adjust the size, shape, color, and other attributes of the specified boundary position 32, and thereby highlight the display. Specifying of an object of alteration is not limited to this, and it may be performed by the cursor position of a mouse cursor and a click operation.

The alteration unit 176 then receives specification of the direction of move and the amount of move. The moving direction and the amount of move are associated with the direction of rotation of a mouse wheel and the amount of rotation thereof, respectively, for example. In this case, when the operator rotates the mouse wheel by a certain amount in the upper direction, the alteration unit 176 interprets it as indicating that it has been specified to move the boundary position 32 by a given distance in the upper direction. The direction of move and the amount of move are not limited to the foregoing, and may be assigned to the directions of the arrow keys on a keyboard and to the number of key presses thereof, respectively.

Then, as illustrated in FIG. 4A, the alteration unit 176 alters, in response to the instructions of alteration, the annular level of the boundary position from and to positions at which the addresses have been defined (composition points). The following describes a situation in which: the position of a composition point 40 that the boundary position 32 passes is (h1,d1); the direction of move is the upper direction; and the amount of move is "20." In this case, the alteration unit 176 moves the position (h1,d1) of the composition point 40, along which the boundary position 32 passes, for 20 addresses in the upper direction, for example. That is, the alteration unit 176 adds 20 to the value of the position of the composition point 40 in the longitudinal direction, so that the position of the composition point 40 becomes (h1+20,d1). Consequently, the alteration unit 176 alters the position of the boundary position 32 in the longitudinal direction to h1+20. The alteration unit 176 further draws a boundary line that connects to the boundary position 32 after the alteration. For example, the alteration unit 176 calculates the shortest path between the composition point 40 and a composition point 41. In this case, the alteration unit 176 obtains a path that is the shortest path between the composition point 40 after the alteration and the composition point 41 and that passes along the initial contours. The alteration unit 176 then draws the boundary line that connects the composition point 40 and the composition point 41, so as for the boundary line to pass along the obtained shortest path.

The calculating unit 172 then recalculates the information in accordance with the alteration made by the alteration unit 176. For example, when such information as the average values of motion index included in a two-dimensional region with the boundary position 32 as the boundary line, the volume of a three-dimensional region with the boundary position 32 as the boundary line, and the like has been calculated, the calculating unit 172 recalculates such information.

The generator 174 then regenerates the image (for example, a rendering image) in accordance with the alteration made by the alteration unit 176. The display controller 175 then displays, on the regenerated image, the information about the first region of interest. Consequently, on the monitor 13, the rendering image in FIG. 4A and the time-changing curves in FIG. 4B are displayed.

As illustrated in FIG. 4B, the display controller 175 displays the time-changing curves of the moving distance D by a graphic chart by using the three-dimensional medical image data after having altered the boundary position, for example. Consequently, a situation in which graph values of the three regions corresponding to the basal area are changed depending on the alteration of the boundary position 32 is made understandable. In the same manner, the volume information on the RV is also changed.

As in the foregoing, the alteration unit 176 receives instructions from the operator and alters the boundary position in response to the instructions. Then, in accordance with the alteration made by the alteration unit 176, the generator 174 regenerates the image, and the display controller 175 displays, on the regenerated image, the information about the first region of interest. Thus, the user can alter the annular level of the boundary position by an intuitive operation, and is enabled to check the situations in front and behind the boundary position that correspond to the alteration thereof and to interactively observe changes in the volume and in the motion index.

FIG. 5 is a flowchart for explaining the processing of the ultrasonic diagnostic apparatus in the first embodiment.

As illustrated in FIG. 5, in the ultrasonic diagnostic apparatus 1, the obtaining unit 171 obtains three-dimensional medical image data obtained by photographing a given area of an object (Step S101). For example, the obtaining unit 171 obtains, for at least one heartbeat, three-dimensional medical image data obtained by photographing at least a part of the heart as a given area.

Subsequently, the calculating unit 172 defines a plurality of regions of interest on a group of three-dimensional medical image data (Step S102). For example, the calculating unit 172 defines a plurality of regions of interest including the RV, the right-ventricular inflow portion, and the right-ventricular outflow portion, by segmentation of boundaries based on boundary detection means concerning the RV and the connected tissue as a whole or means of manually setting boundary positions.

The calculating unit 172 calculates information about at least one of the volume and the motion index on each of the regions of interest from the three-dimensional medical image data (Step S103). For example, the calculating unit 172 defines identification information (addresses) that identifies respective positions on a plurality of positions (composition points) representing the outline of the RV in the three-dimensional medical image data on which a plurality of regions of interest have been defined. The calculating unit 172 then performs tracking of the positions of a plurality of composition points in a plurality of pieces of ultrasonic image data included in the group of ultrasonic image data by performing processing that includes pattern matching by using the ultrasonic image data on which the composition points have been defined and other ultrasonic image data. The calculating unit 172 then calculates, by using the positions of the composition points in pieces of ultrasonic image data included in each group of ultrasonic image data, the motion index representing the motions of tissue for the respective pieces of ultrasonic image data.

The setting unit 173 defines the first region of interest on the regions of interest by at least a single boundary position defined on at least one region of interest out of the regions of interest (Step S104). For example, the setting unit 173 receives, on a plurality of regions of interest defined by the calculating unit 172, the input that specifies a boundary position from the operator. The setting unit 173 then defines, as the first region of interest, the region included in the boundary position specified by the received input. As a result, the setting unit 173 divides the regions of interest into the first region of interest and the second region of interest other than the first region of interest.

The generator 174 generates, from the three-dimensional medical image data, an image that includes the regions of interest and in which the first region of interest and the second region of interest other than the first region of interest are distinguished from each other (Step S105). For example, the generator 174 performs SR processing on the three-dimensional medical image data in which a plurality of regions of interest are divided into the first region of interest and the second region of interest, and generates rendering images.

The display controller 175 displays the information about the first region of interest out of the information calculated by the calculating unit 172, on the image (Step S106). For example, the display controller 175 converts the information including at least one of the volume and the motion index calculated by the calculating unit 172 into color codes, and performs the mapping thereof on the image generated by the generator 174. For example, the display controller 175 displays this image on the monitor 13 as the moving image data for one heartbeat.

The alteration unit 176 receives instructions from the operator and alters the boundary position in response to the instructions, and updates the output (Step S107). For example, the alteration unit 176 receives instructions from the operator and alters a boundary position in response to the instructions. Then, in accordance with the alteration made by the alteration unit 176, the generator 174 regenerates the image, and the display controller 175 displays, on the regenerated image, the information about the first region of interest.

As in the foregoing, in the ultrasonic diagnostic apparatus 1 in the first embodiment, the obtaining unit 171 obtains three-dimensional medical image data obtained by photographing an area of an object including a plurality of regions of interest that are connected. The calculating unit 172 calculates information about at least one of the volume and the motion index on a given region from the three-dimensional medical image data. The setting unit 173 defines, in a region in which a plurality of regions of interest are connected, the first region of interest and the second region of interest other than the first region of interest, by at least a single boundary position defined on the regions of interest. The generator 174 generates, from the three-dimensional medical image data, an image that includes a plurality of regions of interest and in which the first region of interest and the second region of interest are distinguished from each other. The display controller 175 displays, on the image, the information about the first region of interest out of the information calculated by the calculating unit 172. Consequently, the ultrasonic diagnostic apparatus 1 in the first embodiment can facilitate the comprehension of a situation around a boundary of a region of interest defined on a three-dimensional image.

For example, the ultrasonic diagnostic apparatus 1 updates, along with the alteration of a boundary position, the information about the first region of interest near the boundary position that has been altered. Hence, the ultrasonic diagnostic apparatus 1 makes it possible to observe changes in output (such as volume or motion index) at the same time as altering the boundary position while checking the valid range as the region of interest on a three-dimensional display of analysis result. Consequently, even when the boundary position of an annulus area is hard to recognize because the image quality is inadequate, or even when individual cases assume a complicated shape near the annulus area, the ultrasonic diagnostic apparatus 1 makes it possible to determine an adequate boundary position while comprehending the situation of the whole region of interest. As a result, the accuracy of luminal volume output, and the adequacy of wall-motion index output on a local region near the annulus are improved.

Furthermore, in the ultrasonic diagnostic apparatus 1, the setting unit 173 defines a boundary position so as for the boundary position to pass any of a plurality of positions representing the outline of at least a part of a given area, for example. The alteration unit 176 then alters the boundary position so as for the boundary position to pass any of the positions. Consequently, the ultrasonic diagnostic apparatus 1 enables easily alteration of the boundary position between the first region of interest and the second region of interest.

Modification of First Embodiment

In the above-described first embodiment, a situation of altering the annular level of the boundary position 32 by changing the boundary line has been explained. The embodiment, however, is not limited to this. For example, to reflect in detail differences in shape in individual cases, the position of a point included in the boundary position may be altered.

Figure 6:
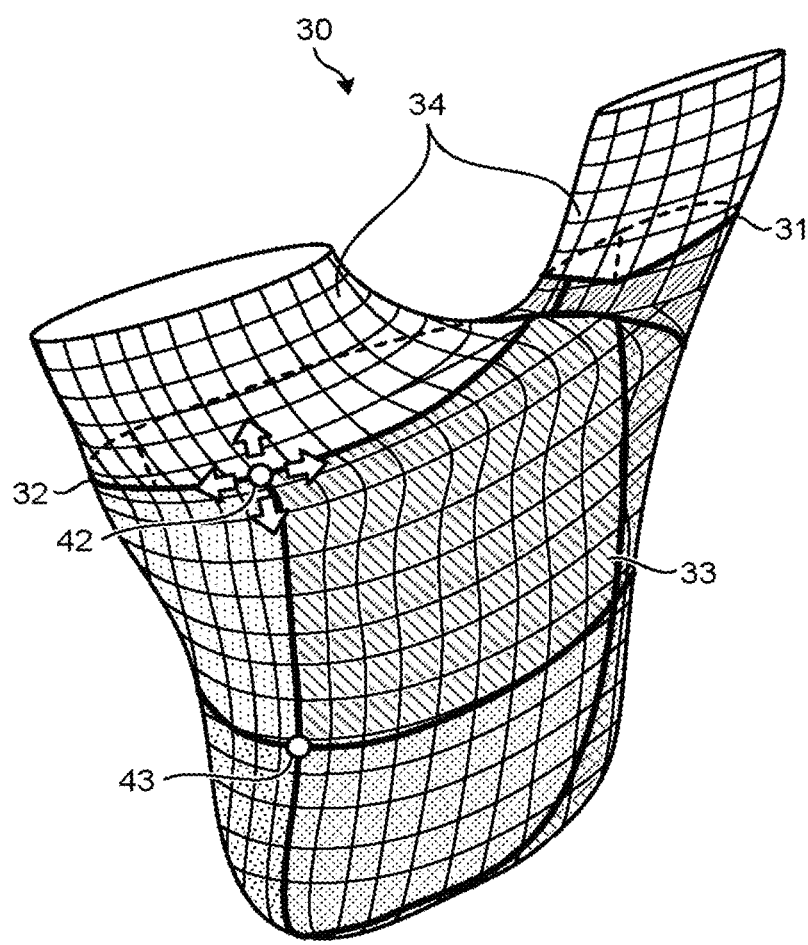
FIG. 6 is a diagram for explaining the processing of an alteration unit according to a modification in the first embodiment.

FIG. 6 is a diagram for explaining the processing of the alteration unit 176 according to a modification of the first embodiment. In FIG. 6, described is a situation of altering a vertex 42 of a segment present on the boundary position 32 in the connected region 30.

For example, in the alteration unit 176, the vertex 42 is specified as an object of alteration by the cursor position of the mouse cursor and click operation. The alteration unit 176 then receives specification of the direction of move and the amount of move. For example, the directions of move and the amounts of move are assigned to the directions of the arrow keys of a keyboard and to the numbers of key presses thereof, respectively. In this case, the operator presses down the arrow key of any desired direction any desired number of times, so that the alteration unit 176 receives the direction of move and the amount of move of the vertex 42. The alteration unit 176 then shifts, in response to the instructions of alteration, the vertex 42 between positions at which the addresses have been defined (composition points). The following describes a situation in which the position of vertex 42 that the boundary position 32 passes along is (h2,d2), the direction of move is the right direction, and the amount of move is "a." In this case, the alteration unit 176 moves the position (h2,d2) of the vertex 42, which the boundary position 32 passes, by "a" addresses in the right direction, for example. That is, the alteration unit 176 adds "a" to the value of the position of the vertex 42 in the circumferential direction, and makes the position of the vertex 42 into (h2,d2+a). Consequently, the alteration unit 176 alters the position of the vertex 42 in the circumferential direction to d2+a. Furthermore, the alteration unit 176 draws a boundary line between the vertex 42 after the alteration and a vertex connected thereto. For example, the alteration unit 176 calculates a shortest path between the vertex 42 and a vertex 43. The alteration unit 176 then draws a boundary line that connects the vertex 42 and the vertex 43 while taking the obtained shortest path.

As in the foregoing, the alteration unit 176 makes alterable the position of a vertex included in the boundary position, and thereby enables reflecting in detail differences in shape in individual cases.

Other Embodiments

The embodiment may be implemented in various different forms other than that in the foregoing embodiment.
Configuration without Alteration Unit 176

The configuration explained in the first embodiment is merely an example, and the ultrasonic diagnostic apparatus 1 does not necessarily need to include the alteration unit 176, for example.

That is, the ultrasonic diagnostic apparatus 1 distinctly displays the first region of interest that is defined on a 3D image and on which the analysis result is displayed, and the second region of interest that is the regions outside thereof. By being displayed in the foregoing manner, the user can easily comprehend, relative to the heart as a whole, the size of the region the analysis result of which is currently displayed, or the situation of the positional relation between the current boundary position and the tricuspid valve (or pulmonary valve), for example.
Application to Image Processing Apparatus The functions described in the first embodiment are not limited to being applied to a medical diagnostic imaging apparatus, and are also applicable to an image processing apparatus, for example.

FIG. 7 is a block diagram illustrating an example of the configuration of an image processing system according to other embodiments. As illustrated in FIG. 7, the image processing system in the other embodiments includes an image processing apparatus 200, a medical diagnostic imaging apparatus 300, and a picture-archiving apparatus 400. The respective apparatuses illustrated in FIG. 7 have been enabled to perform communication with one another directly or indirectly via, for example, an in-hospital local area network (LAN) 5 installed within a hospital. For example, when the image processing system is implemented with a picture archiving and communication system (PACS), the respective apparatuses transmit and receive medical image data and the like to and from one another in accordance with digital imaging and communications in medicine (DICOM) standard.

In FIG. 7, the medical diagnostic imaging apparatus 300 photographs three-dimensional medical image data, and stores the photographed three-dimensional medical image data into the picture-archiving apparatus 400, for example. The medical diagnostic imaging apparatus 300 corresponds to an ultrasonic diagnostic apparatus, an X-ray diagnostic apparatus, an X-ray computed tomography (CT) apparatus, a magnetic resonance imaging (MRI) apparatus, a single photon emission computed tomography (SPECT) apparatus, a positron emission tomography (PET) apparatus, a SPECT- CT apparatus in which a SPECT apparatus and an X-ray CT apparatus are integrally combined, a PET-CT apparatus in which a PET apparatus and an X-ray CT apparatus are integrally combined, a PET-MRI apparatus in which a PET apparatus and an MRI apparatus are integrally combined, or a group of apparatuses that includes two or more of the foregoing apparatuses, for example.

The picture-archiving apparatus 400 is a database that archives medical image data. Specifically, the picture-archiving apparatus 400 stores three-dimensional medical image data generated by the various medical diagnostic imaging apparatuses 300 into storage of the picture-archiving apparatus 400 and keeps the data. The three-dimensional medical image data archived in the picture-archiving apparatus 400 is kept in association with supplementary information such as patient IDs, test IDs, device IDs, and series IDs.

The image processing apparatus 200 is a workstation, a personal computer (PC), or the like that a doctor or a laboratory technician who works in the hospital uses to view medical images, for example. The operator of the image processing apparatus 200 performs search using a patient ID, a test ID, a device ID, a series ID, and other information, and obtains necessary three-dimensional medical image data from the picture-archiving apparatus 400. Alternatively, the image processing apparatus 200 may receive three-dimensional medical image data directly from the medical diagnostic imaging apparatus 300.

The image processing apparatus 200 includes an input unit 201, a communication unit 202, a display 203, storage 210, and a controller 220. The input unit 201, the communication unit 202, the display 203, the storage 210, and the controller 220 are connected to one another.

The input unit 201 is a keyboard, a trackball, a pointing device such as a mouse or a pen tablet, or another device, and receives the input of various operations for the image processing apparatus 200 from the operator. When a mouse is used, the input with a mouse wheel can be performed. When a pen tablet is used, the input by flick operation and swipe operation can be performed. The communication unit 202 is a network interface card (NIC) or the like, and performs communication with other devices. The display 203 is a monitor, a liquid crystal panel, or the like, and displays a variety of information.

The storage 210 is a hard disk and a semiconductor memory device, for example, and stores therein a variety of information. The storage 210 stores therein a plurality of processing that the controller 220 performs, for example.

The controller 220 is an electronic circuit such as a central processing unit (CPU) or a micro processing unit (MPU), or an integrated circuit such as an application specific integrated circuit (ASIC) or a field programmable gate array (FPGA), for example, and performs the control of the image processing apparatus 200 as a whole.

The controller 220 includes the same processing units as the obtaining unit 171, the calculating unit 172, the setting unit 173, the generator 174, and the display controller 175. That is, in the controller 220, the same processing unit as the obtaining unit 171 obtains three-dimensional medical image data obtained by photographing an area of an object including a plurality of regions of interest that are connected. The same processing unit as the calculating unit 172 calculates information about at least one of the volume and the motion indices on a given region from the three-dimensional medical image data. The same processing unit as the setting unit 173 defines, in a region in which a plurality of regions of interest are connected, the first region of interest and the second region of interest other than the first region of interest, by at least a single boundary position defined on the regions of interest. The same processing unit as the generator 174 generates, from the three-dimensional medical image data, an image that includes a plurality of regions of interest and in which the first region of interest and the second region of interest are distinguished from each other. The same processing unit as the display controller 175 displays, on the image, the information about the first region of interest out of the information calculated by the same processing unit as the calculating unit 172. Consequently, the image processing apparatus 200 can facilitate the comprehension of a situation around a boundary of a region of interest defined on a three-dimensional image.

In the above-described embodiments, for example, the respective constituent elements of the devices and apparatuses illustrated are functionally conceptual, and do not necessarily need to be configured physically as illustrated. That is, the specific forms of distribution or integration of the devices and apparatuses are not limited to those illustrated, and the whole or a part thereof can be configured by being functionally or physically distributed or integrated in any form of units, depending on various types of loads, usage conditions, and the like. Furthermore, the whole of or a part of the various processing functions performed in the respective devices and apparatuses can be implemented by a CPU, and a program executed by the CPU, or implemented as hardware by wired logic. The CPU is one example of processing circuitry. For example, the ultrasonic diagnostic apparatus includes the control circuitry as processing circuitry. The control circuitry obtains three-dimensional medical image data obtained by photographing an area of an object. The control circuitry defines a setting region on the three-dimensional medical image data. The control circuitry divides the setting region into a region of interest and a region other than the region of interest by at least a single boundary position. The control circuitry configured to generate, from the three-dimensional medical image data, an image in which the region of interest and the region other than the region of interest are distinguished from each other. The control circuitry calculates information about at least one of a volume of and a motion index of the region of interest. The control circuitry displays the calculated information for the region of interest in the image.

The area to which the above-described image processing method is applied is not limited to the heart, and may be internal organs such as the liver.

In the above-described embodiments, the situations in which the embodiments are applied to the WMT have been explained. However, the embodiments are not limited to this. That is, the embodiments are widely applicable to situations of altering the boundary of a region of interest defined on the surface of an area of a photographic subject included in volume data. The surface of the region of the photographic subject may be the surface (contours) of an internal organ of the photographic subject or may be the body surface. In this case, the surface of the photographic subject may be detected by any conventional technology. In particular, when the embodiments of the present application are applied to an internal organ, it is a preferred application example that, with a plurality of connected tumors regarded as a single region of interest, the volumes of the tumors are simultaneously analyzed while the boundary position among the tumors are altered.

The image processing method described in the foregoing embodiments and modification can be implemented by executing a previously prepared image processing program on a computer such as a personal computer and a workstation. This image processing program can be distributed via a network such as the Internet. The image processing program can also be recorded on a computer-readable recording medium such as a hard disk, a flexible disk (FD), a compact disc read only memory (CD-ROM), a magnetic optical disc (MO), or a digital versatile disc (DVD), and executed by being read out from the recording medium by the computer.

As in the foregoing, according to at least one of the described embodiments, the boundary of a region of interest in a three-dimensional image can be adjusted easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic imaging apparatus, comprising:
control circuitry configured to:
obtain three-dimensional medical image data obtained by acquiring an area of a tissue;
define a setting region on the three-dimensional medical image data, the setting region including a right ventricle, a right-ventricular inflow portion, and a right-ventricular outflow portion;
divide the setting region into a region of interest (ROI) corresponding to the right ventricle and a region other than the ROI by an annular boundary position in at least one of the right-ventricular inflow portion and the right-ventricular outflow portion;
generate, from the three-dimensional medical image data, an image in which the ROI and the region other than the ROI are distinguished from each other;
calculate information about at least one of a volume of and a motion index of the ROI;
display the image in which the ROI and the region other than the ROI are distinguished from each other;
display the calculated information on the ROI in the image,
receive instructions for altering the annular boundary position from an operator on the image,
alter the annular boundary position, based on the received instructions from the operator, so as to alter the ROI,
regenerate, based on the altered annular boundary position, a new image having the altered ROI, and
display information about at least one of the volume and the motion index on the altered ROI in the regenerated new image.

2. The medical diagnostic imaging apparatus according to claim 1, wherein the control circuitry is further configured to recalculate the information based on the altered ROI, and display the recalculated information on the altered ROI.

3. The medical diagnostic imaging apparatus according to claim 2, wherein the control circuitry is further configured to define the annular boundary position so the annular boundary position passes any of a plurality of positions representing an outline of at least a part of the area, and alter the annular boundary position so the annular boundary position passes any of the plurality of positions.

4. The medical diagnostic imaging apparatus according to claim 1, wherein the control circuitry is further configured to
obtain, for at least one heartbeat, three-dimensional medical image data obtained by photographing at least a part of a heart as the area, and
calculate the information by processing including pattern matching between pieces of three-dimensional medical image data included in the three-dimensional medical image data for at least one heartbeat acquired.

5. The medical diagnostic imaging apparatus according to claim 1, wherein the control circuitry is further configured to display the setting region and the ROI with respective color codes different from each other.

6. The medical diagnostic imaging apparatus according to claim 1, wherein the control circuitry is further configured to display the ROI with a color code based on the information and display the region other than the ROI with a wire frame.

7. The medical diagnostic imaging apparatus according to claim 1, wherein the three-dimensional medical image data obtained by the control circuitry is three-dimensional ultrasonic image data generated by transmission and reception of ultrasonic waves.

8. An image processing apparatus, comprising:
control circuitry configured to:
obtain three-dimensional medical image data obtained by acquiring an area of a tissue;
define a setting region on the three-dimensional medical image data, the setting region including a right ventricle, a right-ventricular inflow portion, and a right-ventricular outflow portion;
divide the setting region into a region of interest (ROI) corresponding to the right ventricle and a region other than the ROI by an annular boundary position in at least one of the right-ventricular inflow portion and the right-ventricular outflow portion;
generate, from the three-dimensional medical image data, an image in which the ROI and the region other than the ROI are distinguished from each other;
calculate information about at least one of a volume of and a motion index of the ROI;
display the image in which the ROI and the region other than the ROI are distinguished from each other;
display the calculated information on the ROI in the image,
receive instructions for altering the annular boundary position from an operator on the image,
alter the annular boundary position, based on the received instructions from the operator, so as to alter the ROI,
regenerate, based on the altered annular boundary position, a new image having the altered ROI, and
display information about at least one of the volume and the motion index on the altered ROI in the regenerated new image.

9. An image processing method, comprising:
obtaining three-dimensional medical image data obtained by acquiring an area of a tissue;
defining a setting region on the three-dimensional medical image data, the setting region including a right ventricle, a right-ventricular inflow portion, and a right-ventricular outflow portion;
dividing the setting region into a region of interest (ROI) corresponding to the right ventricle and a region other than the ROI by an annular boundary position in at least one of the right-ventricular inflow portion and the right-ventricular outflow portion;

generating, from the three-dimensional medical image data, an image in which the ROI and the region other than the ROI are distinguished from each other;

calculating information about at least one of a volume of and a motion index of the ROI;

displaying the image in which the ROI and the region other than the ROI are distinguished from each other;

displaying the calculated information on the ROI in the image, receiving instructions for altering the annular boundary position from an operator on the image, altering the annular boundary position, based on the received instructions from the operator, so as to alter the ROI, regenerating, based on the altered annular boundary position, a new image having the altered ROI, and displaying information about at least one of the volume and the motion index on the altered ROI in the regenerated new image.

* * * * *